United States Patent [19]

Charuest et al.

[11] Patent Number: 4,635,623

[45] Date of Patent: Jan. 13, 1987

[54] BRACE FOR AN ARTICULATING LIMB

[75] Inventors: George M. Charuest, Montreal-North; Lawrence P. Coughlin, Pointe Claire, both of Canada

[73] Assignee: J. E. Hanger Limited, Montreal, Canada

[21] Appl. No.: 555,889

[22] Filed: Nov. 28, 1983

[30] Foreign Application Priority Data

Oct. 24, 1983 [CA] Canada ............................ 439564

[51] Int. Cl.⁴ ................................................. A61F 3/00
[52] U.S. Cl. ................................. 128/80 C; 128/80 G
[58] Field of Search ................... 128/80 F, 80 C, 80 R, 128/80 A, 87, 80 G; 2/22, 24

[56] References Cited

U.S. PATENT DOCUMENTS

| Re. 30,501 | 2/1981 | Almeida | 128/80 C |
|---|---|---|---|
| 575,199 | 1/1897 | Autenrieth . | |
| 1,092,836 | 4/1914 | Hart . | |
| 1,635,798 | 7/1927 | Morris . | |
| 2,195,024 | 3/1940 | Bullock . | |
| 3,194,233 | 7/1965 | Peckham . | |
| 3,387,305 | 6/1968 | Shafer . | |
| 3,581,741 | 6/1971 | Rosman | 128/80 C |
| 3,669,105 | 6/1972 | Castiglia | 128/80 C |
| 3,785,372 | 1/1974 | Craig | 128/80 C |
| 4,241,730 | 12/1980 | Helfet | 128/80 C |
| 4,487,200 | 12/1984 | Feanny et al. | 128/80 F |
| 4,493,316 | 1/1985 | Reed et al. | 128/80 C |

*Primary Examiner*—C. Fred Rosenbaum
*Assistant Examiner*—Karen Kaechele
*Attorney, Agent, or Firm*—Russell, Georges, Breneman, Hellwege & Yee

[57] ABSTRACT

The invention relates to a brace used for anterior cruciate insufficiency. The brace is comprised of a femoral engaging component means for securing the femoral engaging component to a limb, a proximal lateral femoral bar fixed to the femoral engaging component and extending downwardly to a proximal femoral lateral position, a proximal medial femoral bar fixed to the femoral engaging component and adapted to extend over the anterior of the thigh to a proximal medial femoral position, a tibial engaging component means for securing the tibial engaging component to a limb, a proximal lateral tibial bar fixed to the tibial engaging component and extending upwardly therefrom to a proximal lateral tibial position, a proximal medial tibial bar fixed to the tibial engaging component and extending upwardly therefrom to a proximal medial tibial position, a medial joint connecting the proximal ends of the proximal medial femoral bar and the proximal medial tibial bar, a lateral joint connecting the proximal ends of the proximal lateral femoral bar and the proximal medial tibial bar, said joints adapted to rotate only through the same horizontal axis as the limb when the brace is applied.

5 Claims, 6 Drawing Figures

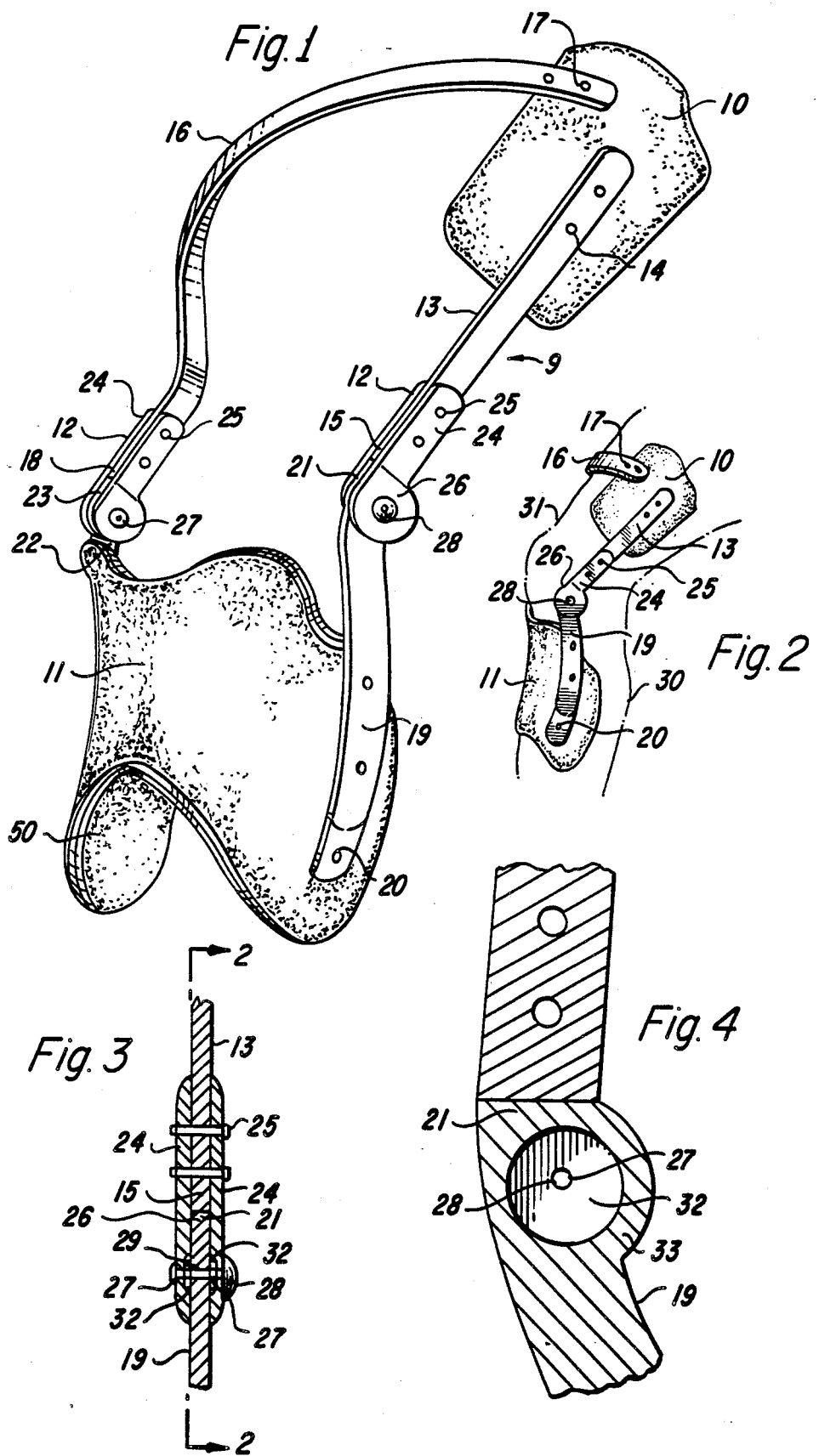

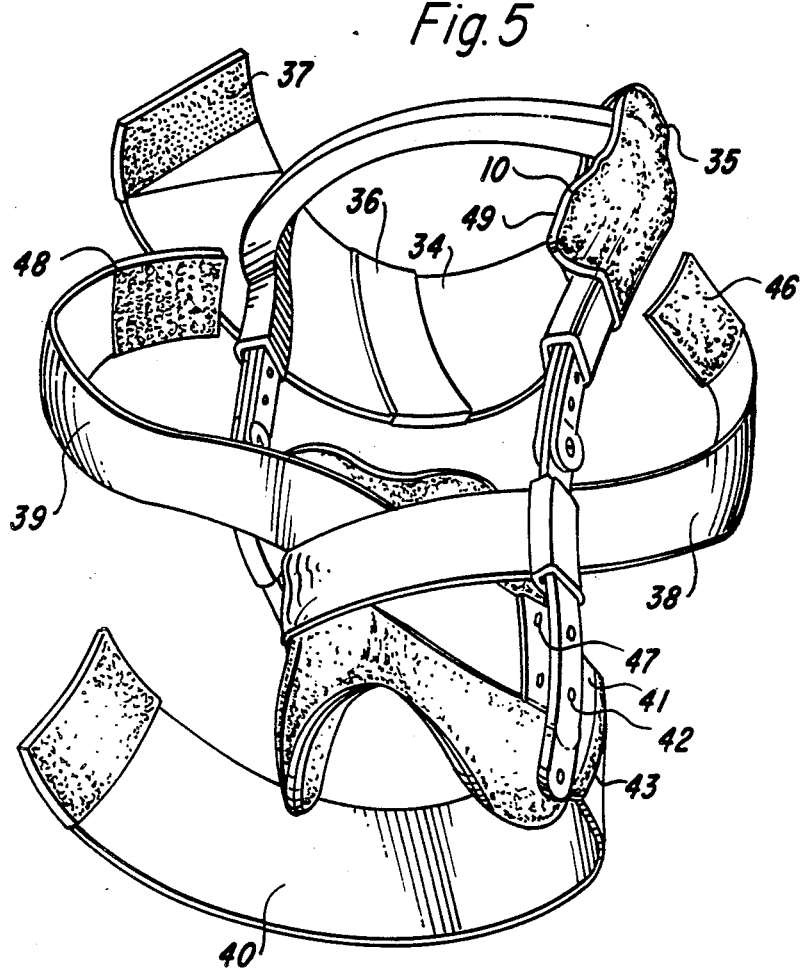
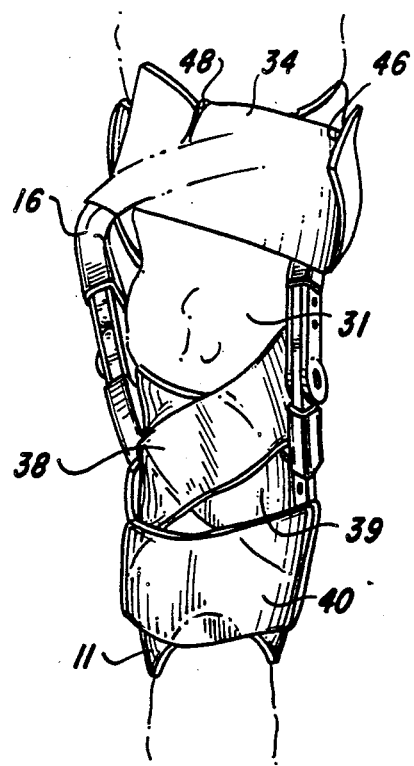

BRACE FOR AN ARTICULATING LIMB

The present invention relates to braces. In particular, the brace is used for anterior cruciate insufficiency. The brace can also be useful for use by athletes playing football to prevent knee injuries.

The articulation of the knee joint between the distal femur, the lower extension of the femur and the proximal tibia, the upper extension of the tibia about a horizontal axis also involves a rotation between the distal femur and proximal tibia.

Any substantial, lateral, medial, posterior or anterior motion between the distal femur and proximal tibia will result in knee ligament injuries.

The maximum rotation between the distal femur and proximal tibia occurs during the last 15° to 20° of knee extension. It is within this margin that most knee injuries and ligament strains will be suffered.

Previous anterior cruciate braces have been designed with an adjusting posterior strap to limit full extension. A constant problem with prior anterior cruciate braces has been durability as there is tremendous stress and pull on the post strap. These braces had full plastic thigh and calf cuffs to distribute enough holding power to control the knee. These features made the braces very hot, heavy and bulky and allowed very little room for muscle contraction/relaxation and muscle growth, both of which may tend to atrophy the leg.

Other braces which included a stop placed within the joint between the thigh portion and calf portion of the knee brace to control knee extension had no solid anterior counter force. Such braces had only crossing elastic straps on the anterior tibia which may easily give way to the pressure caused by the mechanical stops at the joint. The pre-tibial bar also caused excessive pressure with resulting pain as the knee attempted to go into full extension.

It is a primary object of the present invention to provide a brace which is relatively light which will limit anterior-posterior excursion of the tibia when the knee is in flexion utilizing a tibial mold and a joint designed to eliminate a predetermined extension of the knee.

The pre-molded tibial member in conjunction with the extension stop limits rotational deviation, the anti-rotation resistance is augmented by bilateral derotation straps. The pre-molded tibial member also eliminates the discomfort on the pre-tibial area as the knee attempts to go into full extension by more evenly distributing the pre-tibial pressure over a larger surface area.

The brace controls medial lateral injuries by having a three point pressure system which is necessary on all orthapedic knee devices. With the brace at a determined stop below normal full extension of the knee, the valgus duration (medial) is resisted by the pre-molded tibial member and the bilateral derotation straps. The main component of anterior cruciate insufficiency is the anterior lateral subluxation of the tibial plateau which primarily occurs between 20° and full extension. By preventing full extension this rotatory component of the instability can be controlled. Also by the design of the tibial mold tibial rotation can also be controlled. The tibial mold by being custom molded to each patient prevents any inferior-superior pistoning of the brace.

The same principle applies to a varus (lateral) duration, since the most common of knee injuries is that of side to side motion or a combination of lateral and medial and posterior or anterior movements, this brace because of the versatility of its design can limit all of the above undesirable movements.

In one embodiment of the invention there is provided a brace for controlling the movement of an articulated joint about a single axis, comprising a femoral engaging component, means for securing the femoral engaging component to a limb, a proximal lateral femoral bar having a distal end fixed to the femoral engaging component and extending downwardly to a proximal femoral lateral position, a proximal medial femoral bar having a distal end fixed to the femoral engaging component and adapted to extend over the anterior of the thigh to a proximal medial femoral position, a molded tibial engaging component molded to fit the anterior tibial portion of the calf, means for securing the tibial engaging component to a limb, a proximal lateral tibial bar having a distal end fixed to the tibial engaging component and extending upwardly therefrom to a proximal lateral tibial position, a proximal medial tibial bar having a distal end fixed to the tibial engaging component and extending upwardly therefrom to a proximal medial tibial position, a medial joint connecting the proximal ends of the proximal medial femoral bar and the proximal medial tibial bar, a lateral joint connecting the proximal ends of the proximal lateral femoral bar and the proximal medial tibial bar, said joints adapted to rotate only through the same horizontal axis as the limb when the brace is applied.

In a preferred embodiment of the invention the tibial engaging component is molded to fit the anterior tibial portion of the calf.

In another embodiment at least one joint is comprised of a head plate fixedly attached near the lower end of the femoral bar, said head plate having a receiving portions having an aperature therein, the tibial bars having an aperature therein coaxial with the aperature in the receiving portions is adapted to fit into said receiving portion; when the ends of the femoral bar and tibial bar are in contact and aligned, a pin receivable in said aperatures, and means for securing said pin in said aperatures.

In another embodiment of the invention, the joint includes an extension stop preventing extension of the joint past a selected angle of extension.

In another embodiment of the invention derotation straps are attached medially and laterally to the tibial engaging component, the other end of the derotation straps are adapted to be secured to the means for securing the tibial engaging component.

The invention is illustrated by way of example in the accompanying drawings which form part of this application and in which:

FIG. 1 is a perspective view of the limb engaging anterior femoral section and anterior tibial section and the joints between these sections;

FIG. 2 is a side elevation of the brace of FIG. 1 shown mounted at the knee joint of the leg showing the brace as it appears when looking at the outside of the leg;

FIG. 3 is a sectional fragmentary elevation taken along the line 1—1 of FIG. 1 illustrating the structure on a larger scale than that of FIG. 1;

FIG. 4 is a cross-section view taken along the line 2—2 of FIG. 3 illustrating the structure at the joint;

FIG. 5 is a perspective illustration of the brace of FIG. 1 showing in addition, elasticized bands for attaching the anterior femoral section and the anterior tibial section to the leg, and derotation straps between the anterior tibial section and the femoral section;

FIG. 6 is a front view of the brace of FIG. 5 applied to a limb about the knee.

The drawings illustrate and the principles of the invention are described in relation to kneee braces, but it will be apparent to those skilled in the art that the principles described herein may be utilized in relation to the elbow joint.

Referring to the drawings, there is shown in Figure 1 a brace 9 having a femoral engaging component 10 and a tibial engaging component 11. These components respectively designed to engage the leg respectively above the knee and below the knee are joined by bars to joints 12. The femoral engaging component 10 which is preferably made of aluminium has a proximal lateral femoral bar 13 riveted 14 thereto at a distal end of the bar. The proximal lateral femoral bar 13 is adapted to extend down the outside of the thigh to a proximal end 15, a point on a horizontal axis through the knee when the brace is applied. The femoral engaging component 10 also has a proximal medial femoral bar 16 riveted 17 at a distal end of the bar to the femoral engaging component 10. The proximal medial femoral bar 16 is contoured to follow the anterior portion of the thigh downwardly and then medially to end proximal 18, a point on a horizontal axis through the knee when the brace is applied.

The tibial engaging component 11 is composed of a shell of high density polyethylene or like material which is heated and molded to fit the cast of the leg of the wearer. the tibial engaging component 11 has a proximal lateral tibial bar 19 fastened thereto by copper rivets 20 at a distal end of the bar. The proximal lateral tibial bar 19 is adapted to extend upwardly and inwardly following the lateral path of the proximate tibial portion of the calf to proximal end 21 a point on a horizontal axis through the knee when the brace is applied. The tibial engaging component 11 also has a proximate medial tibial bar 22 oppositely disposed to the proximate lateral tibial bar 19 and fastened to the tibial engaging component by copper rivets at a distal end of the bar. The proximate medial tibial bar 22 extends upwardly following the lateral medial axis of the proximate tibial portion of the calf to proximal end 23, a point on the horizontal axis through the knee when the brace is applied. The interior of the tibial engaging component 11 is lined with a synthetic foam padding 50.

The proximal lateral femoral bar 13 and proximate medial femoral bar 16 have head plates 24 fastened to either side of the respective bars by steel rivets 25. The head plates 24 extend beyond the proximal ends 15 and 18 of the proximal lateral femoral bar 13 and the proximate medial femoral bar 16 to respectively receive the proximal ends 21 and 23 of the proximal lateral tibial bar 19 and the proximal medial tibial bar 22, to form joints 12. The receiving portion 26 of the head plates 24 contain aperatures 27 adapted to receive stainless steel expanding rivets 28. The proximate lateral tibial bar 19 and the proximate medial tibial bar 22 contain aperatures 29 corresponding with aperatures 27 of head plates 24 adapted to receive respective stainless steel expanding rivets 28 to form joints 12 when the proximal end 21 of proximal lateral tibial bar 19 engages the proximal end 15 of proximal lateral femoral bar 13 and the proximal end 23 of proximal medial tibial bar 22 engages the proximal end 18 of proximal medial femoral bar 16.

When the basic elements of the brace described in FIG. 1 are applied to the leg as shown in FIG. 2, the femoral engaging component 10 engages the outside of the thigh. The proximal lateral femoral bar 13 extends down the outside of the thigh. Head plates 24 are fastened to the proximal lateral femoral bar 13 by rivets 25. The proximal medial femoral bar 16 is also fastened to femoral engaging component 10 by rivets 17. The proximal medial femoral bar 16 follows closely the anterior portion of the thigh downwardly towards the proximal medial end of the femur until the end 18 of the proximal medial femoral bar is oppositely disposed to the end 15 of the proximal lateral femoral bar 13. The tibial engaging component 11 is molded to fit the cast of the wearer. The tibial engaging component 11 fits snugly against anterior proximal tibial portion of the calf 30 from just below the kneecap 31. The upper part of tibial engaging component 11 on either side of the kneecap 31 flares upwardly. The lower part of tibial engaging component 11 flares downwardly laterally and medially to contact the sides of the calf 30. As seen in FIG. 2 the tibial engaging component 12 covers the upper front and sides of calf 30. The proximal lateral tibial bar 19 extends upwardly from the tibial engaging component 11 to which it is fastened by rivets 20.

The proximal lateral tibial bar 19 extends upwardly following the lateral path of the proximate tibial portion of the calf 30 to end 21. End 21 of the proximate tibial portion is received in the receiving portion 26 of head plates 24 and is fastened thereto by stainless steel expanding rivet 28. As seen in FIG. 1, the proximate medial tibial bar 22 is also fastened by rivets to the tibial engaging component 11 and the end 23 of the proximal medial tibial bar 22 is fastened into the receiving portion 26 of head plates 24 by stainless steel expanding rivets 28.

As seen in FIG. 3, head plates 24 are fastened by steel rivets 25 to the proximal portion of the proximal lateral femoral bar 13. The receiving portion 26 of the head plates 24 contains aperatures 27. The head plates 26 are bent slightly outwardly in the area of aperatures 27 in order to receive washers 32 hereinafter described. The proximate lateral tibial bar 19 has an aperature 29. When aperature 29 and aperature 27 are aligned, the end 21 of proximate lateral tibial bar 19 and the end 15 of proximate lateral femoral bar 15 are in end to end contact. The aperatures 29 and 27 are retained and fastened into alignment by stainless steel expanding rivet 28. Washers 32 are adapted to be received between the outsides of the proximate lateral tibial bar 19 around aperature 27 and between the inside of the enlarged head portion 33 of head plates 24.

In FIG. 4, the proximate portion of the proximal lateral femoral bar 13 is shown engaging the proximal portion of proximal lateral tibial bar 19. The end 15 of proximal lateral femoral bar 13 rests against the end 21 of proximal lateral tibial bar 19. The aperature 27 and washers 32 of proximal lateral tibial bar 19 are shown in and on the enlarged head portion 33 of proximal lateral tibial bar 19. The stainless steel expanding rivet 28 is shown in aperature 27. The angle of extension formed by the proximal lateral femoral bar 13 and the proximal lateral tibial bar 19 may be controlled by changing the configuration of ends 15 and 19 of proximal lateral femoral bar 13 and the proximal lateral tibial bar 19. By controlling the configuration of the ends 15 and 19 the angle of extension desired by the doctor may be limited for instance to 150°, or may be limited to 180° for an athlete wearing the brace merely as a protective measure. The angle of extension controlled by joints 12 is made as substantially identical as possible on each joint 12 of brace 9, although these angles of extension will vary from brace to brace as mentioned above.

FIG. 5 shows the brace of FIG. 1 together with means for attaching the brace to the limb and additional straps to prevent rotation of the thigh and calf relative to one another. An elasticized band 34 is sewn onto a covering applied to the femoral engaging component 10. A velcro backing 35 is applied to the covering on the back of femoral engaging component 10. The elasticized band 34 is adapted to be stretched around the thigh when the brace 9 is in place, to retain the femoral engaging component 10 firmly against the thigh. The elasticized band 32 has velcro fasteners 36 and 37 sewn against a backing. These fasteners are adpated to receive velcro fasteners on the medial derotation strap 38 and lateral derotation strap 39 referred to later. An elasticized band 40 having a strengthened end 41 is attached by rivets 42 to the lateral edge of the tibial engaging component 11. Immediately adjacent the strengthened end 41 is a velcro strip 43 adapted to receive a mating velcro strip 44 sewn to backing of elasticized band 40 when the elasticized band 40 is stretched around the back of the calf and over the tibial engaging component 11. Elasticized band 40 retains the molded tibial engaging component 11 of brace 9 firmly against the proximal anterior tibial portion and calves of the leg.

One end of the medial derotation strap 38 is fastened to the medial side of the tibial engaging component 11 by rivets 45. The other end of the medial derotation strap 38 contains a velcro fastener 46. The medial derotation strap 38 which is made of elasticized material is pulled over the upper front of the tibial engaging component 11 under the proximal lateral tibial bar 19 around the back of the leg just above the knee where the medial derotation strap is fastened to the elasticized band 36 on the femoral engaging component 10. One end of the lateral derotation strap 39 is fastened to the lateral side of the tibial engaging component 11 by rivets 47. The other end of the lateral derotation strap 39 contains a velcro fastener 48. The lateral derotation strap 39 which is made of elasticized material is pulled over the upper front of the tibial engaging component 11 under the proximal medial tibial bar 22 around the back of the leg just above the knee where the lateral derotation strap is fastened to velcro backing on the elasticized band 34 holding the femoral engaging component 10 in place.

The proximal lateral femoral bar 13, proximal medial femoral bar 16, proximal lateral tibial bar 19 and the proximal medial tibial bar 22 are all made of aluminium and are covered with rubber hosing where these bars may contact the leg in order to prevent contusions or scratching of the leg. Furthermore, the femoral engaging component 10 has a soft rubber pad 49 applied to its interior to protect the leg.

As shown in FIG. 6 the brace 9 is placed on the leg so that the molded tibial engaging component 11 sits against the anterior proximal tibial portion of the leg just below the kneecap 31. The elasticized band 40 is firmly stretched around the back of the calf and over the front of the tibial engaging component 11. The velcro fastener 44 on the end of elasticized band 40 is then fastened to the velcro strip 43 on the front face of the tibial engaging component 11. With the mating ends 18 and 23 of the proximal medial femoral bar 16 and the proximal medial tibial bar 22 in full contact and the ends 15 and 24 of the proximal lateral femeral bar 13 and proximal lateral tibial bar 19 in full contact the femoral engaging component 11 is placed firmly against the thigh. The elasticized band 34 is extended around the back of the thigh over the top portion of the proximal medial femoral bar 16 and then the velcro fastener 37 on the elasticized band 34 is fastened to the velcro backing 35 of the femoral engaging component 10. The lateral derotation strap 39 is then placed over the top front part of the tibial engaging component 11 and under the proximal medial tibial bar 22 around the back of the leg above the knee then extended and fastened to velcro backing on the femoral engaging component 10. The medial derotation strap 38 is then placed over the top front part of the tibial engaging component 11 and under the proximal lateral tibial bar 19 around the back of the leg above the knee then extended and fastened to the velcro strip 36 of elasticized band 34.

It will be recognized by those skilled in the art that certain elements disclosed herein may be substituted for by equivalents without departing from the scope of the invention.

What is claimed is:

1. A knee brace for controlling the movement of a knee joint of a wearer having an anterior cruciate deficiency about an axis, comprising a femoral engaging component, means for securing the femoral engaging component to the leg of the wearer above the knee, a proximal lateral femoral bar having a distal end fixed to the femoral engaging component and extending downwardly to a proximal femoral lateral position, a proximal medial femoral bar having a distal end fixed to the femoral engaging component and extending downwardly to a proximal femoral medial position, a tibial engaging component molded to fit the anterior tibial portion of the calf, means for securing the tibial engaging component to the leg of the wearer below the knee, a proximal lateral tibial bar having a distal end fixed to the tibial engaging component and extending upwardly therefrom to a proximal lateral tibial position, a proximal medial tibial bar having a distal end fixed to the tibial engaging component and extending upwardly therefrom to a proximal medial tibial position, a medial joint connecting the proximal ends of the proximal medial femoral bar and the proximal medial tibial bar, a lateral joint connecting the proximal ends of the proximal lateral femoral bar and the proximal lateral tibial bar, and at least one of said joints including an extension stop adapted to limit the extension of the joint beyond the point at which abnormal internal rotation between the distal femur and proximal tibia occurs while otherwise permitting normal extension of the joint to occur, said molded tibial engaging component being adapted to minimize abnormal tibial rotation in conjunction with said extension stop.

2. The brace of claim 1 in which the tibial engaging component is molded to fit below the patella and flare upwardly on either side of the patella while extending downwardly and laterally from the patella to cover substantially the upper front and side portions of the calf.

3. The brace of claim 1 in which at least one of said lateral or medial joints is comprised of a head plate fixedly attached near the lower end of the femoral bar, said head plate having a receiving portion, the head plate having aligned coaxial apertures therein, the top of the tibial bar being adapted to fit in said receiving portion, the top of the tibial bar having an aperture coaxial with the apertures in the receiving portion when the ends of the femoral bar and tibial bar are in contact, a pin receivable in said apertures and said aperture of said tibial bar to retain said tibial bar in said receiving portion, means for securing said pin in said aperture, and the abutting ends of the tibial and femural bars cooperating to form an extension stop which prevents extension of the joint beyond the point at which rotation between the distal femur and proximal tibia occurs.

4. The brace of claim 1 wherein said proximal medial femoral bar is adapted to extend over the anterior of the thigh to a proximal medial femoral position.

5. The brace of claim 1 wherein said extension stop is adapted to prevent the extension of the knee through the last 15 degrees of knee extension.

* * * * *